US00PP11690P

United States Patent [19]

Walden

[11] Patent Number: Plant 11,690

[45] Date of Patent: Dec. 12, 2000

[54] SHRUB ROSE PLANT NAMED 'JACBOW'

[75] Inventor: John K. Walden, Thousand Oaks, Calif.

[73] Assignee: Bear Creek Gardens, Inc., Medford, Oreg.

[21] Appl. No.: 09/234,790

[22] Filed: Jan. 20, 1999

[51] Int. Cl.[7] ..... A01H 5/00

[52] U.S. Cl. ..... Plt./102

[58] Field of Search ..... Plt./101, 102, 106, Plt./107, 108, 141

*Primary Examiner*—Howard J. Locker

*Attorney, Agent, or Firm*—Klarquist Sparkman Campbell Leigh & Whinston, LLP

[57] ABSTRACT

A shrub rose plant having pointed ovoid buds; a unique, bicolor flower; a full, globular habit; dark green, glossy foliage; resistance to powdery mildew; and a light, sweet, spicy fragrance.

1 Drawing Sheet

The present invention relates to a new and distinct variety of rose plant of the shrub class which was originated by me by crossing 'JACship' (U.S. Plant Pat. No. 7,948), with 'SAValife' (U.S. Plant Pat. No. 5,482).

The primary objective of this breeding was to produce a new rose variety having pointed ovoid buds; a unique, bicolor flower; a full, globular habit; dark green, glossy foliage; disease resistance; and fragrance. The objective was substantially achieved, along with other desirable improvements, as evidenced by the following unique combination of characteristics that are outstanding in the new variety and that distinguish it from its parents, as well as from all other varieties of which I am aware:

1. Very novel tan, yellow, pink, mauve color blend of flower;
2. Pointed ovoid buds;
3. Globular plant habit;
4. Dark green, glossy foliage;
5. Disease resistance to powdery mildew; and
6. Light, sweet, spicy fragrance.

JACbow's seed hip is round in shape, measuring ¾–1" in diameter, between Yellow-Green Group 144A and 144B when immature, immediately prior to the color change as the hip matures.

Asexual reproduction of this new variety by cuttings and budding, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—'JACship' (U.S. Plant Pat. No. 7,948).

*Pollen parent.*—'SAValife' (U.S. Plant Pat. No. 5,482).

Classification:

*Botanical.*—*Rosa hybrida.*

*Commercial.*—Shrub.

FLOWER

Observations made from specimens grown in a greenhouse environment at Somis, Calif. on Nov. 10, 1998, and at Atlanta, Ga.

Blooming habit: Recurrent.

Bud:

*Size.*—⅞ inches long when the petals start to unfurl.

*Form.*—The bud form is short, pointed ovoid.

*Color.*—When sepals first divide, the bud color is Red Group 47A with a Yellow Group 2A triangle at petal base. When half blown, the upper sides of the petals are Greyed-Orange Group 173B with tones of Greyed-Purple 186C and Greyed-Purple 186C near distal ½ of petal, with a Yellow Group 2A ⅜" spot at petal base. The lower sides of the petals are near Greyed-Orange Group 171C with a ⅜" Yellow Group 2A spot at petal base which often extends up the midrib of the petal.

*Sepals.*—Color: Yellow-Green Group 144A and Greyed-Purple Group 183B where exposed to direct sun. Surface texture: Rough, with small glandular structures. There are three normally appendaged sepals. There are two unappendaged sepals with hairy edges.

*Receptacle.*—Color: Yellow-Green Group 144A and Greyed-Purple Group 183B where exposed to sun. Shape: Funnel. Size: Medium (¼" long×⅜" wide). Surface: Smooth.

*Peduncle.*—Length: Medium (averaging 1⅛"). Surface: Rough; glandular. Color: Light green (Yellow-Green Group 146C), and bronzy (Greyed-Purple Group 183A). Strength: Stiff; erect.

Bloom:

*Size.*—Medium. Average open size is 2¾".

*Borne.*—Singly and several together in small clusters having pyramidal shape of three to five buds.

*Stems.*—Strength: Normal. Short, average length is 9".

*Form.*—When first open: High centered. Permanence: Outer petal edges curl slightly.

*Petalage.*—Number of petals under normal conditions: 20–25.

*Color.*—The upper sides of the petals are near Greyed-Orange Group 173C with a ⅜" Yellow Group 3A spot at petal base. The reverse sides of the petals are near Greyed-Orange Group 173B mixed with Yellow Group 4C. The base of each petal has a ⅜" spot Yellow Group 3A. The major color on the upper side is Greyed-Orange Group 173C.

*Discoloration.*—At the end of the first day: Near Greyed-Orange Group 173C with five outer guard petals darker in color (Greyed-Red Group 181C). At the end of the third day: Greyed-Red Group 181D. The finish color of the flower is between Red-Purple Group 60C and 60D in general tonality, before petals drop off.

*Fragrance.*—Slight, but sweet and spicy.

Petals:

*Texture.*—Leathery.

*Shape.*—Round.

*Form.*—Edges slightly quilled.

*Arrangement.*—Imbricated; shingle-like. Petaloids in the center: Few; large.

*Persistence.*—Petals drop off cleanly before drying.

*Lastingness.*—On the plant: Long (9–10 days). As a cut flower: Fair (6–7 days).

Reproductive parts:

*Anthers.*—Size: Medium. Quantity: Many. Color: Yellow Group 11B. Arrangement: Regular around styles.

*Filaments.*—Color: Yellow Group 13B.

*Pollen.*—Color: Gold yellow, Yellow-Orange Group 20A.

*Styles.*—Color: Green-White Group 157B with some reddish tone.

*Stigmas.*—Color: Greyed-Yellow Group 160C.

Plant:

*Form.*—Shrub.

*Growth.*—Vigorous; upright; globular.

*Mature plant.*—Height is 3½ feet, and width is 3½ feet.

Foliage: Number of leaflets on normal med-stem leaves: Seven.

*Size.*—(3¼" long×2¼" wide.).

*Quantity.*—Abundant.

*Color.*—New foliage: Upper Surface: Yellow-Green 146A with Greyed-Purple 184A leaf margin. Lower Surface: Greyed-Purple 184A rapidly changing to near Yellow-Green Group 148B. Old foliage: Upper Surface: Near Green Group 139A. Lower Surface: Yellow-Green Group 147B.

*Shape.*—Pointed oval.

*Texture.*—Upper side: Glossy; smooth.

*Edge.*—Serrated.

*Serration.*—Single.

*Petiole rachis.*—Color: Green Group 137C.

*Petiole underside.*—With prickles.

*Stipules.*—Long (⅞"); serrated.

*Disease resistance.*—Resistant to mildew and tolerant of blackspot under normal growing conditions at Somis, Calif. and Atlanta, Ga.

Wood:

*New wood.*—Color: Greyed-Purple Group 183A rapidly changing to Yellow-Green 144B. Bark: Smooth.

*Old wood.*—Color: Yellow-Green Group 146B. Bark: Smooth.

Prickles:

*Quantity.*—On main canes from base: Ordinary. On laterals from main canes: Ordinary.

*Form.*—Medium; angled downward.

*Color when young.*—Greyed-Purple Group 185A.

Small prickles:

*Quantity.*—On main stalks: None. On laterals: None.

I claim:

1. A new and distinct variety of rose plant of the shrub class, substantially as herein shown and described, characterized particularly as to novelty by its pointed ovoid buds; a unique, bicolor flower; a full, globular habit; dark green, glossy foliage; resistance to powdery mildew; and a light, sweet, spicy fragrance.

* * * * *

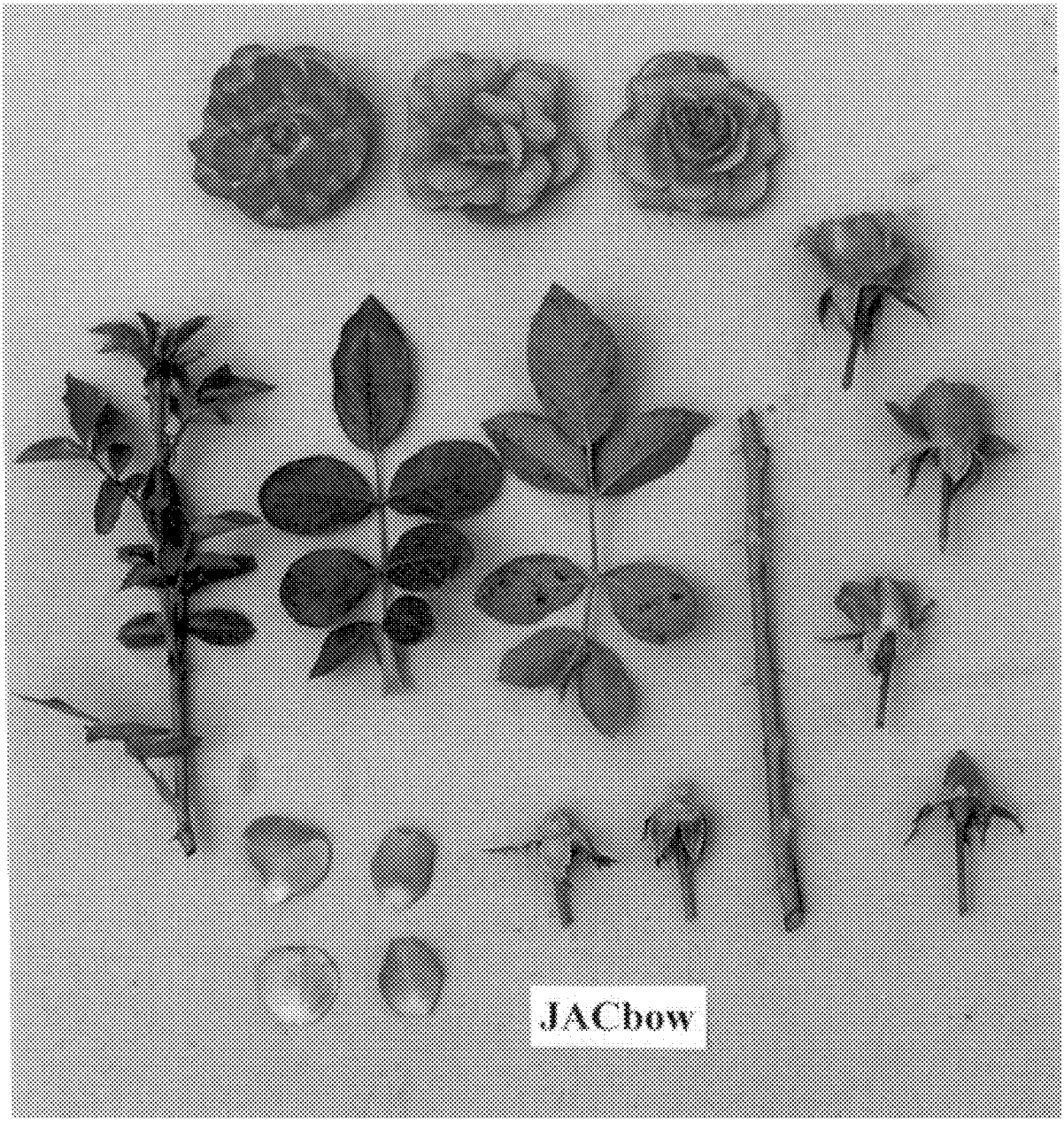
JACbow

UNITED STATES PATENT AND TRADEMARK OFFICE

CERTIFICATE OF CORRECTION

PATENT NO. : PP 11,690
DATED : December 12, 2000
INVENTOR(S) : John K. Walden

It is certified that error appears in the above-identified patent and that said Letters Patent is hereby corrected as shown below:

Column 3,
Line 27, please change "med-stem" to -- mid-stem --, as shown on Page 4, line 26, of the application.

Signed and Sealed this

Twelfth Day of February, 2002

*Attest:*

*Attesting Officer*

JAMES E. ROGAN
*Director of the United States Patent and Trademark Office*